US011185276B2

(12) United States Patent
Cox (10) Patent No.: US 11,185,276 B2
(45) Date of Patent: Nov. 30, 2021

(54) VISION EXAMINATION SYSTEM WITH IMPROVED VISUALLY EVOKED POTENTIAL WAVEFORMS

(71) Applicant: Diopsys, Inc., Pine Brook, NJ (US)

(72) Inventor: Laurie A. Cox, Pine Brook, NJ (US)

(73) Assignee: DIOPSYS, INC., Pine Brook, NJ (US)

( * ) Notice: Subject to any disclaimer, the term of this patent is extended or adjusted under 35 U.S.C. 154(b) by 1012 days.

(21) Appl. No.: 15/635,736

(22) Filed: Jun. 28, 2017

(65) Prior Publication Data

US 2017/0296089 A1 Oct. 19, 2017

Related U.S. Application Data

(63) Continuation of application No. 13/947,915, filed on Jul. 22, 2013, now Pat. No. 9,717,465.

(60) Provisional application No. 61/674,052, filed on Jul. 20, 2012.

(51) Int. Cl.
*A61B 5/378* (2021.01)
*A61B 5/00* (2006.01)
*A61B 5/398* (2021.01)
*A61B 3/10* (2006.01)

(52) U.S. Cl.
CPC ............... *A61B 5/378* (2021.01); *A61B 3/10* (2013.01); *A61B 5/398* (2021.01); *A61B 5/6821* (2013.01); *A61B 5/7235* (2013.01); *A61B 5/7282* (2013.01); *A61B 5/6814* (2013.01); *F04C 2270/041* (2013.01)

(58) Field of Classification Search
None
See application file for complete search history.

(56) References Cited

U.S. PATENT DOCUMENTS

| | | | | |
|---|---|---|---|---|
| 4,387,723 A * | 6/1983 | Atlee, III | ............. | A61B 5/1106 600/547 |
| 4,896,677 A * | 1/1990 | Kaneko | ................ | A61B 5/0436 600/509 |
| 5,003,986 A * | 4/1991 | Finitzo | ................ | A61B 5/04845 600/544 |
| 6,466,817 B1 * | 10/2002 | Kaula | .................. | A61B 5/0488 600/546 |
| 2001/0049480 A1 * | 12/2001 | John | ...................... | A61B 5/121 600/559 |
| 2003/0144601 A1 * | 7/2003 | Prichep | ................ | A61B 5/7203 600/544 |
| 2005/0251056 A1 * | 11/2005 | Gribkov | ............... | A61B 5/0452 600/509 |
| 2006/0084879 A1 * | 4/2006 | Nazarian | ................ | A61B 5/721 600/500 |
| 2009/0326867 A1 * | 12/2009 | Watson | ............. | A61B 5/14551 702/180 |

(Continued)

*Primary Examiner* — Matthew Kremer
(74) *Attorney, Agent, or Firm* — Ostrolenk Faber LLP (57) ABSTRACT

A method and a system are disclosed for extracting important signal information. The method examines a group of signals obtained from testing of a patient's nervous system and finds a signal area of interest. Once a cluster of signals that all have the area of interest is found—the system concludes that the area of interest is located and validated. Signals that are not within the cluster are rejected and the signals within the cluster are signal-averaged to yield a signal-averaged waveform. The signal averaged waveform represents the results of the test.

18 Claims, 5 Drawing Sheets

(56) References Cited

U.S. PATENT DOCUMENTS

2010/0283973 A1\* 11/2010 Derr ...................... A61B 13/00
351/239

\* cited by examiner

VISION EXAMINATION SYSTEM WITH IMPROVED VISUALLY EVOKED POTENTIAL WAVEFORMS

RELATED APPLICATION

This application claims the benefit of U.S. Provisional Patent Appl. Ser. No. 61/674,052 filed on Jul. 20, 2012 and is a continuation of U.S. patent application Ser. No. 13/947,915—the contents of which are incorporated by reference herein.

FIELD OF THE INVENTION

The current invention relates to the field of signal data extraction, more specifically to an improved apparatus and method for extracting signal information from a plurality of signals obtained by VEP testing.

BACKGROUND OF THE INVENTION

Early detection of disease is of utmost importance in improving the odds of successful treatment. However, once a patient presents with disease symptoms, often, the disease is somewhat advanced or established. In order to truly discover a potential problem at earlier stages, asymptomatic patients should be screened for early signs of disease.

Glaucoma and other ocular and nerve-related diseases are among diseases that could potentially be detected at an early stage. There exists in the art a variety of tests that are capable of detecting early onset of glaucoma and other diseases of the nervous system.

Pattern VEP is a well-known diagnostic aid in the detection of glaucoma and other nerve-related diseases. In this test, a patient observes reversing patterns displayed on a screen and such sensory stimulation of the visual field causes Visually Evoked Potentials (VEPs). Electrodes placed on a subject's scalp detect the VEPs.

In diagnosing, and/or screening patients using VEP techniques, a clinician looks for an N75 P100 N135 complex in a resultant waveform. The N75 P100 N135 complex conveys important information about the condition of the nervous cells carrying a nerve impulse.

Pattern Electroretinography (PERG) is a diagnostic tool for ocular disease that is similar to VEP. However, unlike with VEP where signal from the visual cortex is captured at the back of the skull, with PERG signal is collected directly from the retina by way of a sensor placed under the patient's eye. With PERG testing the diagnostically important waveform has an N35-P50-N95 complex.

Typically, each time a pattern displayed on the screen is flipped, a signal is generated. After a specified number of signals is captured, a software program signal averages the plurality of captured signals and produces one waveform which represents the N75 P100 N135 complex or the N35-P50-N95 complex—as the case may be.

One problem with this method of producing a signal-averaged signal is that signals that do not correspond to the N75 P100 N135 complex or to the N35-P50-N95 complex may be included in the signal-averaged waveform. For example, signal artifacts caused by a patient blinking or moving may be erroneously included into the signal-averaged waveform. As a consequence, the sensitivity and specificity of the VEP or PERG test may be diminished or compromised.

SUMMARY OF THE INVENTION

The present invention is directed to a novel method and apparatus for enhancing the accuracy of a signal-averaged waveform that is derived from a plurality of signals. The system identifies a time frame during which an area of interest is expected to occur in a signal ("area of interest" being either a peak or a trough). The system then examines a plurality of signals to determine if the area of interest is present in respective ones of the plurality of signals. Once the area of interest is detected in a respective number of signals during the expected time frame—then the area of interest is validated. For example, if the area of interest is a peak and the expected time frame is between 90 and 120 milliseconds, then when a predetermined number of peaks (e.g. 5 peaks) or a predetermined percentage of peaks is detected in the timeframe between 90 and 120 milliseconds—the system will determine that it located and validated the area of interest. Once such determination is made—peaks that occur outside of the given timeframe (i.e. earlier than 90 msec or later than 120 msec) are disregarded.

The system, as such, identifies signals that are supportive of a waveform of interest and those that are not supportive of a waveform of interest. The signals that are not supportive of a waveform of interest are not included in a signal-averaged test result.

DETAILED DESCRIPTION OF THE INVENTION

Embodiments of the present invention will now be described with reference to the above-identified Drawings. However, the Drawings and the description herein of the invention are not intended to limit the scope of the invention. It will be understood that various modifications of the present description of the invention are possible without departing from the spirit of the invention. Also, features described herein may be omitted, additional features may be included, and/or features described herein may be combined in a manner different from the specific combinations recited herein, all without departing from the spirit of the invention.

Figure 1:
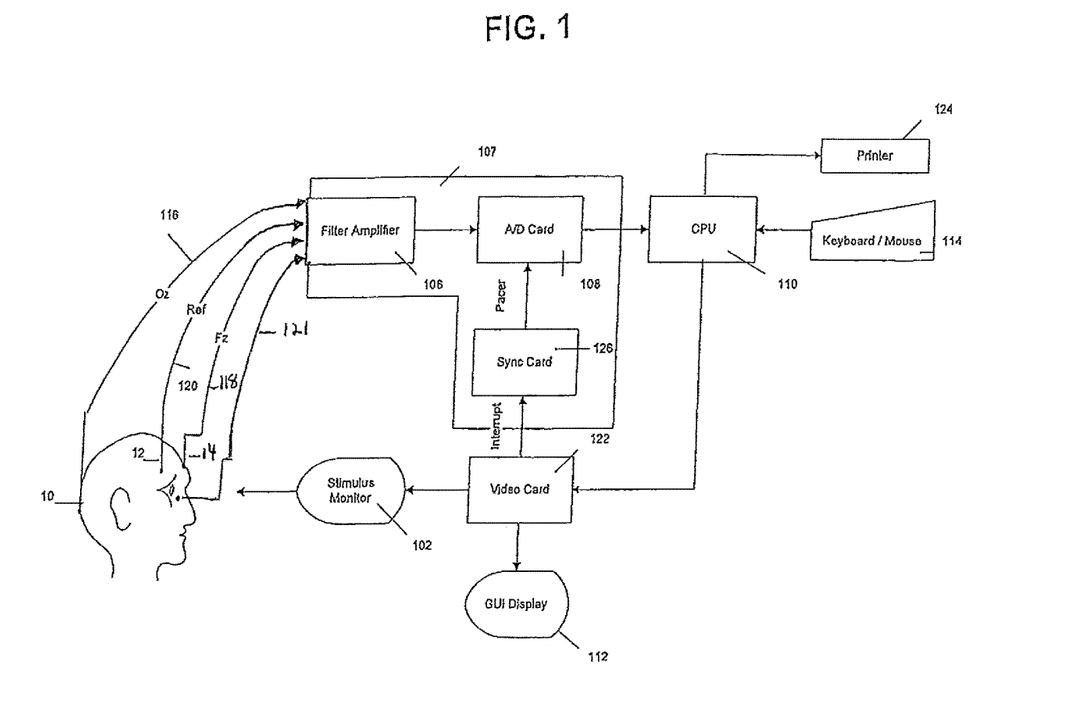
FIG. 1 is a schematic view of a system architecture according to an embodiment of the invention.

Referring to FIG. 1, a system configuration of the hardware components according to an embodiment of the invention is shown. As shown, a display device 102, or stimulus monitor is provided for displaying patterns to a viewer 104. Sensors 10, 12 and 14, such as disposable electrodes, attached non-invasively to a patient's scalp or below the patient's eye detect responses to stimuli generated by the optic nerve or by the retina, respectively. Such responses are amplified, digitized, recorded and analyzed by the data acquisition component 107. Conductors 116, 118 and 120 collect information from sensors 10, 14 and 12 respectively, which are positioned on the scalp of the patient 104 over the visual cortex, the frontal cortex, and the parietal cortex, respectively. Conductors 116, 118 and 120 are connected to the VEP recording and measuring device. Conductor 121, is positioned beneath the eye of a patient is connected to a PERG measuring device.

A VEP or PERG recording and measuring device (or data acquisition component) 107, acquires responses to brain or retina stimuli. The data acquisition component comprises an amplifier 106, which receives signals from sensors 116, 118, 120 and/or 121 and amplifies the VEP/PERG signals. Such amplified signal is then supplied to an analog to digital converter 108 for converting the analog VEP/PERG signals into digital form. The data acquisition component is connected to a central processing unit 110 of a computer for controlling the operations and functions of the VEP/PERG recording and measuring device. The computer has and/or is connected to a digital storage medium for storing signal data and other necessary information. The CPU is connected to a Graphic User Interface (GUI) or monitor 112, which displays data captured by the VEP/PERG recording and measuring device and conveys information concerning the operation of a test being conducted to an operator. Keyboard 114, connected to CPU 110, allows for an operator to input information to the computer relating to a subject being tested. A printer 124 also connected to the CPU allows for test results to be printed out. A visual stimulus-generating device 122 such as a video card is also connected to the CPU and is controlled thereby. Stimulus generating device 122 generates the patterns that are perceived by the patient on monitor 102. Stimulus generating device 102 is connected to the data acquisition component 107 by way of a Sync Card 126. The Sync Card 126, synchronizes the periodic visual stimulus and the sampling rate for recording the VEP/PERG signal responses. Software running on the computer is programmed to carry out the processing steps described herein.

Figure 2:
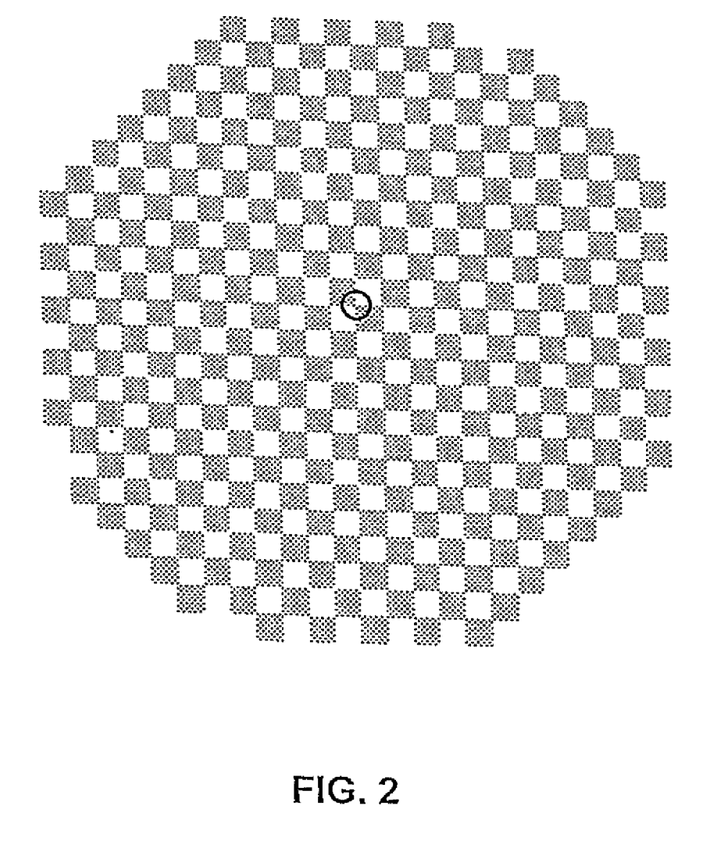
FIG. 2 shows a low contrast checkerboard pattern according to an embodiment of the invention.
Figure 3:
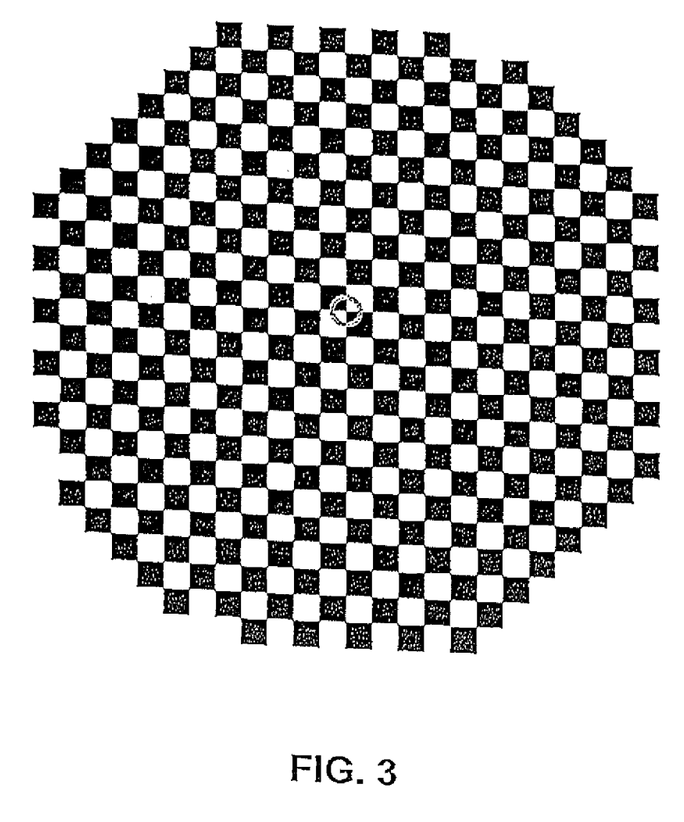
FIG. 3 shows a high contrast checkerboard pattern according to an embodiment of the invention.

FIGS. 2 and 3 show two examples of patterns that are shown to a patient in order to stimulate the retina and the optic pathway. FIG. 2 shows a low contrast, checkerboard pattern, whereas FIG. 3 shows a high contrast pattern. In either case, a "pattern flip" is performed by reversing the light and dark boxes on the checkerboard. It will be understood by one of ordinary skill in the art that other patterns are possible and are within the scope of the current invention.

In diagnosing and or screening patients using VEP techniques, the N75-P100-N135 complex conveys important information about the condition of the retina's ganglion cells and the optic nerve which carries the nerve impulse. The N75-P100-N135 complex, which is well known in the art of VEP, corresponds roughly to the depolarization and repolarization phases of an action potential. Latency or diminished amplitudes of the N75-P100-N135 response may indicate nerve damage such as loss of conduction, for example, due to a myelin sheath deficiency. It is thus, the N75-P100-N135 complex that is the focus of VEP testing. Signal portions that are not associated with the N75-P100-N135 complex are, for the most part, diagnostically uninteresting.

As described, in order to include only signals that are supportive of the N75 P100 N135 complex, the software is trained to disregard artifacts and signals that are not representative of the N75 P100 N135 complex. In one embodiment, the software is trained to analyze two or more frames at a time and signal average them. An automatic cursor placement routine locates the P100 peak for each signal-averaged pair of frames. The P100s are evaluated using a histogram. A cluster found in the range of the expected P100 is identified. If the cluster is comprised of a sufficient percentage of the frames from the entire test, then a P100 has been identified. Frames outside this cluster are not included in the signal-averaged test result. This results in a cleaner and more accurate VEP response—as signal that is not supportive of the P100 is not included in the resultant signal averaged waveform.

For example, given a specific contrast pattern, a P100 peak is expected to occur roughly between 93 and 118 milliseconds. In such a testing environment, the software is trained to generate a histogram or such similar plotting function to identify a cluster of peaks that occur within 93 and 118 milliseconds. If a predetermined number of peaks are identified in the expected time—then the software concludes that the P100 peak has been located and validated. Any peaks that are outside of the expected time frame are rejected and not included into the signal-averaged waveform. In one embodiment of the invention, the expected timeframe for the P100 peak is in a range from 80 to 140 msec. It will be understood by those of ordinary skill in the art that any of various ranges are possible in different embodiments of the invention—all of which are within the teaching of this invention.

In one embodiment of the invention, signal clusters located in two or three (or more) consecutive bins are used to identify N75-P100 complex. Any peaks that are located before or after the specified three (or more) bins are recognized as outliers and they are therefore not included in the signal-averaged waveform. It will be understood that the number of consecutive bins may vary—and they can be more or less than three in different embodiments of the invention.

If an insufficient number of frames are found in a cluster, then the P100 will not be identified. This is important because neural noise alone can tend to create peaks that could be misinterpreted as a P100 response. What results is a more stable P100 response since it is not as effected by random frames which might would tend to shift the true P100 by more or less from test to test.

It will be understood that the latency of a response may be obtained in any of various ways in different embodiments of the invention. For example, rather than examining single frames to detect P100 latencies—the system instead signal averages two or more frames of responses (each resulting from a different stimulus) and it incorporates the latency of the signal averaged waveform as one frame in the bin that has a corresponding latency range. More specifically, assuming that a signal is generated each time a pattern is flipped—the system does not analyze each generated signal to detect P100 peaks—rather the system creates composite signal-averaged waveforms and it analyzes the signal-average waveforms to determine if a P100 peak is present. When a cluster of signal-averaged P100 peaks is identified—the system concludes that the P100 has been located. It will be understood by those of ordinary skill in the art that single frames may be analyzed for P100 peaks and it is not necessary to analyze composites of two or more frames. It will be further understood that composites of more than two signals may analyzed in different embodiments of the invention.

As described, the system identifies a cluster of P100 peaks in order to conclude that the P100 has been located and validated. A cluster may be established in any of various means. In one embodiment of the invention, the system determines a ratio of valid signal to invalid signal and uses the ratio to determine if sufficient number of valid signals were obtained. If a sufficient percentage of response signals is valid—then a cluster has been established. For example, if a waveform of interest contains a P100 peak arriving in the timeframe between 80 to 140 msec, then a signal having such peak within the given timeframe is a "valid signal." Peaks that fall outside of the 80 to 140 msec timeframe are said to be "invalid." After all signals from a complete test have been obtained and stored, the system determines what percentage of signals is valid. If the percentage is above a predetermined percentage value—then a cluster of P100 peaks is established and the P100 is located and validated. If the percentage of valid signals is below a predetermined percentage, then a cluster is not established and the P100 is not validated. In an embodiment of the invention, the predetermined percentage value ranges from 30-50%—but different ranges and different percentage values may be used in different embodiments of the invention.

The software of the invention is programmed to carry out several principal functions for each test. All signals derived from nerve stimuli are stored on a digital storage medium. The software then analyzes the stored signal data to determine if a cluster of signals have been obtained that are supportive of a particular waveform (e.g. a P100 latency). The software then takes two independent signals and signal averages them into a signal averaged waveform. The signal-averaged waveform is then analyzed to detect a P100 peak within a given time frame. The software continues this process until all or a predetermined number of signals obtained is analyzed to identify the P100 (or other area of interest). The software then calculates the number of signals in which the P100 was identified out of the total number of signals obtained for a given test. The software then determines if the percentage of signals in which the P100 was identified is above a predetermined percentage value. If the number is above a predetermined percentage value, then the software concludes that the P100 or other signal area of interest is located and validated. The software then signal-averages all the signals in which the P100 was detected within the given timeframe to yield a resultant signal-averaged waveform which represents the results of a test. Any outlier signals are disregarded and not incorporated into the resultant signal-averaged waveform.

As a result, the inventive system identifies frames that are not supportive of the VEP N75 P100 complex, and removes them from the signal-averaged result. The resulting response has a number of benefits: a good response whether with the expected P100 latency or delayed P100 latency tends to be less noisy (making the P100 easier to identify), and the P100 latency tends to be more stable test after test. Poor responses (whether caused by pathology or patient inattentiveness or poor patient connectivity) can be identified as such, so that an erroneous P100 latency is not calculated.

Figure 4:
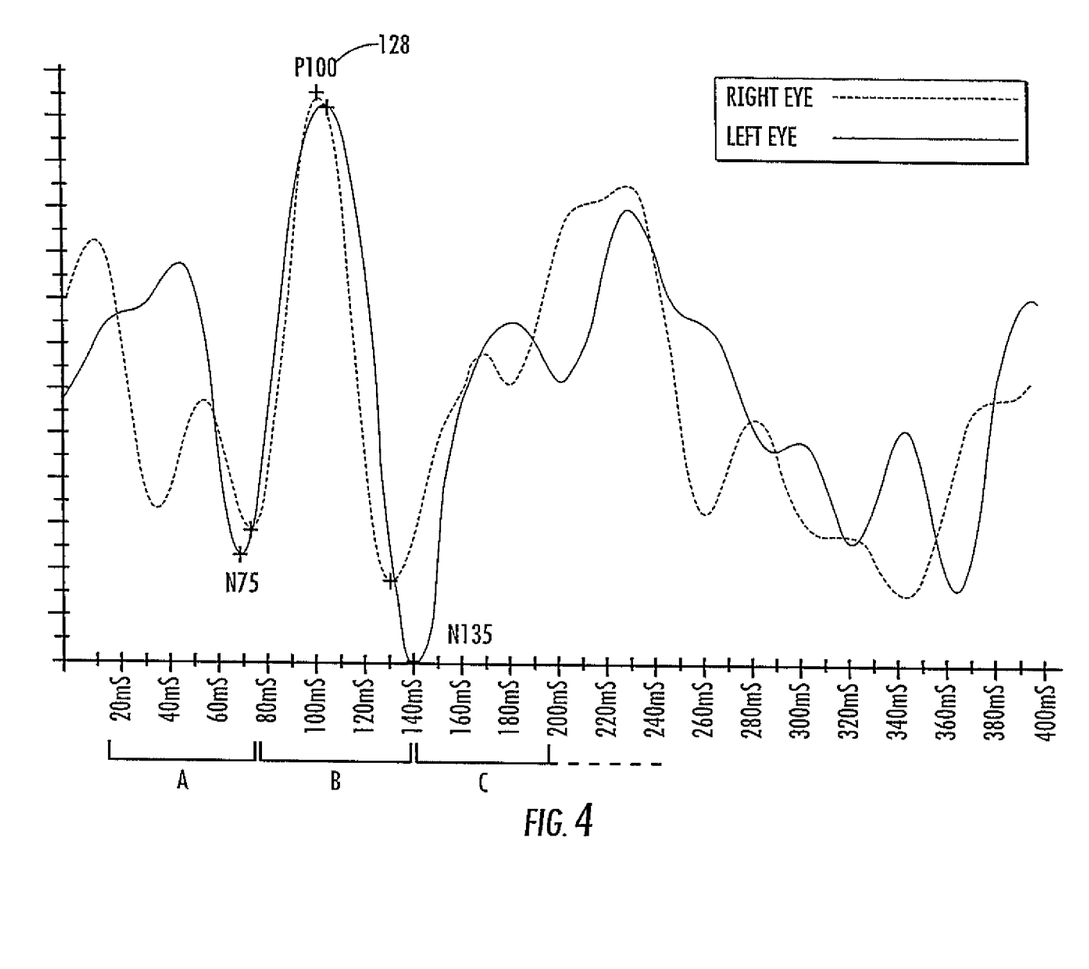
FIG. 4 shows a read-out of two signal-averaged waveforms obtained from a patient's right and left eye, respectively according to an embodiment of the invention.

FIG. 4 shows two signal-averaged waveforms obtained from a patient's right and left eye, respectively. A P100 peak is shown occurring roughly between 85 and 120 msec (time frame B). In this example, a cluster of peaks occurring in timeframe B are identified and included in a signal-averaged waveform. Once a threshold number of signals are detected within timeframe B—a P100 peak is established. Any peak occurring outside of timeframe B (i.e. timeframe A and C), is disregarded and is not included into the final resultant signal-averaged waveform.

Pattern Electroretinography (PERG) is another diagnostic modality used in the detection of glaucoma. PERG is similar to VEP in that signal is generated by stimuli resulting from a patient observing pattern flipping on a screen. However, the signal is captured by a specialized sensor that is placed under the eye of a patient. In testing with PERG, the diagnostically important waveform has an N35-P50-N95 complex. The N35-P50-N95 complex is similar to the expected waveform for VEP except that it is typically smaller in amplitude, and shifted to the left in time. Because the PERG sensor receives stimuli directly from the retina (in contrast to VEP which capture signal at the back of the skull), signal is captured earlier in time as compared to VEP and as a result the N35-P50-N95 complex is shifted left. Consequently, while VEP signal peaks at or around 100 msec, PERG signal peaks at around 50 msec.

In an embodiment of the invention, the system is programmed to identify P50 peaks in a PERG signal. In a similar manner as described with respect to VEP, a time frame during which the P50 is expected to occur is identified. Once a predetermined number of peaks within the expected timeframe is detected—the software concludes that the P50 has been located and validated. For example, in one embodiment of the invention, the software is set to identify peaks arriving between 40 and 60 milliseconds as P50 peaks. Once a cluster of peaks is detected in that timeframe—then the P50 is located. Any peaks that arrive outside of the timeframe (i.e. earlier than 40 or later than 60 msec) are disregarded and they are not included in the resultant signal averaged waveform.

Figure 5:
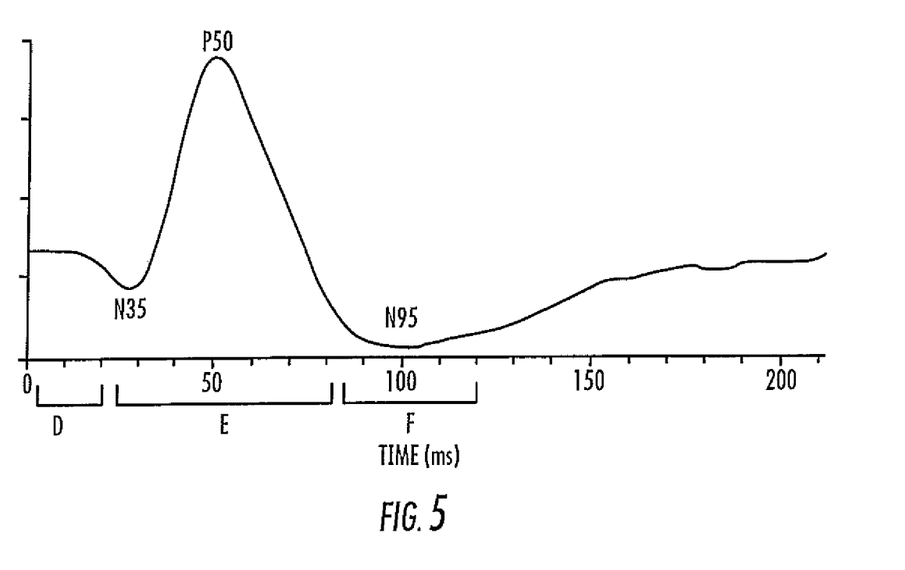
FIG. 5 shows a read-out of a signal-averaged waveform obtained from a patient during PERG testing according to an embodiment of the invention.

FIG. 5 shows a signal-averaged waveform obtained from a patient during PERG testing. A P50 peak is shown occurring roughly between 48 and 52 msec (time frame E). In this example, a cluster of peaks occurring in timeframe E are identified and included in a signal-averaged waveform. Once a threshold number of signals are detected within timeframe E—a P50 peak is established and validated. Any peak occurring outside of timeframe B (i.e. timeframe D and F), is disregarded and is not included into the signal-averaged waveform that represents the test result.

It will be understood that the method and system described herein may be used for any plurality of signals acquired in various testing environments and VEP and PERG are exemplary only.

Having described this invention with regard to specific embodiments, it is to be understood that the description is not meant as a limitation since further modifications and variations may be apparent or may suggest themselves to those skilled in the art. It is intended that the present application cover all such modifications and variations.

The invention claimed is:

1. A vision examination system comprising:
   (a) a computer-operated display device, which displays visual stimuli to a subject;
   (b) a synchronizer, which synchronizes the visual stimuli with a sampling rate;
   (c) one or more sensors, which detect the subject's responses to the stimuli;
   (d) a data acquisition component having an analog to digital converter, which acquires waveforms from the one or more sensors and converts the waveforms to digitized signals;
   (e) a digital storage medium, in which the digitized signals are stored; and
   (f) a computer having a central processing unit (cpu);
   wherein the cpu executes programming which causes the computer to
   (g) generate a plurality of signal averaged waveforms, each signal-averaged waveform being the average of at least two digitized signals;
   (h) analyze each signal-averaged waveform to detect a signal peak and a signal trough in the signal-averaged waveform;

(i) generate a histogram by binning each signal-averaged waveform based upon a latency of the detected signal peak or detected signal trough thereof;

j) from the histogram, select bins within a pre-determined range of a pre-selected expected signal latency;

(k) select the signal-averaged waveforms from the bins selected in step (j); and (l) generate a second digitized signal-averaged waveform from the signal-averaged waveforms selected in step (k).

2. The system of claim 1 wherein the one or more sensors comprise scalp electrodes.

3. The system of claim 2 wherein the detected signal peak is a P100 peak.

4. The system of claim 2 wherein the detected signal peak is a P50 peak.

5. The system of claim 1 wherein the one or more sensors comprise electrodes configured for attachment beneath an eye.

6. The system of claim 5 wherein the detected signal peak is a P100 peak.

7. The system of claim 5 wherein the detected signal peak is a P50 peak.

8. The system of claim 1 wherein the detected signal peak is a P100 peak.

9. The system of claim 1 wherein the detected signal peak is a P50 peak.

10. A vision examination system comprising:

(a) a computer-operated display device, which displays visual stimuli to a subject;

(b) a synchronizer, which synchronizes the visual stimuli with a sampling rate;

(c) one or more sensors, which detect the subject's responses to the stimuli;

(d) a data acquisition component having an analog to digital converter, which acquires waveforms from the one or more sensors and converts the waveforms to digitized signals;

(e) a digital storage medium, in which the digitized signals are stored; and (f) a computer having a central processing unit (cpu); wherein the cpu executes programming which causes the computer to (g) generate a plurality of signal averaged waveforms, each signal-averaged waveform being the average of at least two digitized signals;

(h) analyze each signal-averaged waveform to detect a signal peak and a signal trough in the signal-averaged waveform;

(i) generate a histogram by binning the signal-averaged waveforms based upon a latency of the detected signal peak or detected signal trough thereof;

j) from the histogram, select bins within a pre-determined range of a pre-selected expected signal latency;

(k) select the signal-averaged waveforms from the bins selected in step (j);

(l) calculate a percentage of the signal-averaged waveforms generated at step (g) which were selected at step (k); and (m) if the percentage calculated at step (1) is above a pre-determined value, generate a second digitized signal-averaged waveform from the signal-averaged waveforms selected in step (k).

11. The system of claim 10 wherein the one or more sensors comprise scalp electrodes.

12. The system of claim 11 wherein the detected signal peak is a P100 peak.

13. The system of claim 11 wherein the detected signal peak is a P50 peak.

14. The system of claim 10 wherein the one or more sensors comprise electrodes configured for attachment beneath an eye.

15. The system of claim 14 wherein the detected signal peak is a P100 peak.

16. The system of claim 14 wherein the detected signal peak is a P50 peak.

17. The system of claim 10 wherein the detected signal peak is a P100 peak.

18. The system of claim 10 wherein the detected signal peak is a P50 peak.

* * * * *